(12) United States Patent
Spencer

(10) Patent No.: US 12,220,552 B2
(45) Date of Patent: Feb. 11, 2025

(54) TATTOO TOOL

(71) Applicant: Pursuit of Madness LLC, Las Vegas, NV (US)

(72) Inventor: Austin Spencer, Las Vegas, NV (US)

(73) Assignee: Pursuit of Madness LLC, Las Vegas, NV (US)

( * ) Notice: Subject to any disclaimer, the term of this patent is extended or adjusted under 35 U.S.C. 154(b) by 369 days.

(21) Appl. No.: 17/573,627

(22) Filed: Jan. 11, 2022

(65) Prior Publication Data

US 2022/0218972 A1 Jul. 14, 2022

Related U.S. Application Data

(63) Continuation-in-part of application No. 29/765,718, filed on Jan. 11, 2021, now Pat. No. Des. 972,726.

(60) Provisional application No. 63/146,367, filed on Feb. 5, 2021.

(51) Int. Cl.
*A61M 37/00* (2006.01)

(52) U.S. Cl.
CPC ... *A61M 37/0076* (2013.01); *A61M 2205/273* (2013.01)

(58) Field of Classification Search
CPC ......... A61M 37/0076–0084; A61M 2205/273; A01K 11/00; A01K 11/005; A61B 17/205; A61B 2017/00747; A61B 2017/00769
See application file for complete search history.

(56) References Cited

U.S. PATENT DOCUMENTS

| | | |
|---|---|---|
| 4,665,912 A | 5/1987 | Burton |
| 4,862,772 A | 9/1989 | Piperato |
| D380,046 S | 6/1997 | Domanowski |
| 6,626,927 B1 | 9/2003 | Koplen |
| 7,211,097 B2 | 5/2007 | Carrasco |
| 7,380,480 B1 | 6/2008 | Chen |
| D597,668 S | 8/2009 | Woodruff et al. |
| D686,728 S | 7/2013 | Chen et al. |
| D691,263 S | 10/2013 | Chen et al. |
| D709,196 S | 7/2014 | Greep et al. |
| 8,920,379 B2 | 12/2014 | Lee |
| D743,546 S | 11/2015 | Jayaraj |

(Continued)

OTHER PUBLICATIONS

Authentink, Tebori Tattoos, Sep. 25, 2020, https://web.archive.org/web/20200925013521/https://www.authentink.com/japanese-irezumi/tebori-2/ (Year: 2020).*

(Continued)

*Primary Examiner* — Brigid K Byrd
(74) *Attorney, Agent, or Firm* — Connie R. Masters

(57) ABSTRACT

A tattoo tool is presented that receives a disposable tattoo cartridge and causes the needles of the cartridge to be constantly extended for manual tattooing. The tattoo tool includes a front cartridge-receiver for receiving a tattoo cartridge and a back handle portion. The cartridge-receiver comprises a cartridge-receiving concavity configured to accept the cartridge and to secure the cartridge in a position in which the cartridge needles are extended to reach beyond the cartridge tip and are maintained in this position. Embodiments are presented in which the tool is a single-piece tool. In other embodiments, the tattoo tool is a two-part tool that includes a front cartridge-receiver and a separable handle that can be removably attached.

20 Claims, 9 Drawing Sheets

(56) References Cited

U.S. PATENT DOCUMENTS

| | | |
|---|---|---|
| D766,432 S | 9/2016 | Schuerg |
| D794,194 S | 8/2017 | Schuerg |
| D805,195 S | 12/2017 | Lee |
| D805,197 S | 12/2017 | Lee |
| D805,198 S | 12/2017 | Lee |
| D848,674 S | 5/2019 | Zu |
| D881,385 S | 4/2020 | Tiedeken |
| D903,866 S | 12/2020 | Chen |
| 2004/0116953 A1* | 6/2004 | Dixon ............... A61M 37/0076 606/186 |
| 2014/0358172 A1* | 12/2014 | Lin .................. A61M 37/0076 606/185 |
| 2016/0184572 A1* | 6/2016 | Xiao ................ A61M 37/0076 606/186 |
| 2017/0072178 A1* | 3/2017 | Xiao ................ A61M 37/0084 |
| 2021/0330953 A1* | 10/2021 | Kortenhorst ........... A61B 90/39 |

OTHER PUBLICATIONS

Detroit Free Press, Ancient art tatau on display at Detroit tattoo expo, Mar. 7, 2015, https://www.freep.com/story/news/local/michigan/detroit/2015/03/07/tatau-tattoo-detroit-expo/24575833/ (Year: 2015).*

Non-Final Rejection dated May 24, 2022 of related U.S. Appl. No. 29/765,718.

Notice of Allowance dated Aug. 17, 2022 of related U.S. Appl. No. 29/765,718.

* cited by examiner

TATTOO TOOL

FIELD OF INVENTION

This invention relates generally to a tattooing apparatus, and, more particularly, to a manual or hand poke-type tattoo tool for receiving a disposable needle cartridge.

BACKGROUND OF THE INVENTION

Tattoos, which are body decorations that permanently mark the skin, are becoming increasingly popular. An Ipsos poll in 2019 found that thirty percent of Americans now have at least one tattoo.

In centuries past, all tattooing was manual. Tattooing was performed with a needle attached to a grip, such as by a string, wire, or wrap. The needle was dipped in ink before use.

Now most tattoos are applied by a tattoo machine that uses a needle cartridge which is disposable and hygienic. The needle cartridge is a small plastic casing carrying multiple needles in preferred tattooing needle arrangements, including needle grouping arrangement types such as round liner, round shader, magnum shader, curved magnum shader, and flat shader. The needle grouping is stored within the plastic casing of the cartridge. During the application of the tattoo, a small electric motor of the tattoo machine applies pressure to a piston at the base of the tattoo needle cartridge to force the needle grouping out of the plastic casing. The tattoo needle grouping is rapidly moved out and as the machine extends and retracts the piston.

Though tattoo machines can create a large tattoo in a short time, manual or hand poke tattooing has advantages. Manual tattooing is quieter, less painful, and causes less trauma to the skin, so the healing process is faster.

Traditional manual style tattooing has recently become more popular again. But clients receiving a manual tattoo tend to worry about hygiene if a needle is merely attached to a grip. Additionally, it is a disadvantage to the tattoo artist to be required to take the extra time required to manually attach a needle to a grip for each use.

Thus, there is a need for a tattoo tool for manual tattooing that provides convenience of use and that allows the easy attachment of a disposable cartridge to the tool to minimize the tattoo artist's time required for preparing the tool and to increase hygiene.

BRIEF SUMMARY OF THE INVENTION

The present invention is directed to a tattoo tool for manual tattooing that receives a conventional, disposable tattoo needle cartridge intended for use with a tattoo machine and holds the needle grouping in a constantly extended position. The tool has two portions, a back portion and a front portion. The back portion of the tool comprises a comfortable handle. The front portion of the tool comprises a cartridge-receiver. The cartridge-receiver includes a cartridge-receiving concavity that is functional to accept the cartridge, to secure the cartridge, and to maintain the needles of the cartridge in an extended position. The cartridge-receiving concavity includes a solid bottom floor that compresses the piston at the base of the needle cartridge thereby forcing the needle grouping out of the plastic casing of the cartridge and maintaining the needle grouping in this extended position while the cartridge is disposed within the concavity.

Presented are two tool embodiments (with and without a detachable handle) and two kits including both a tool and one or more cartridges. In the first and second embodiment, the tool is formed as a single piece comprising both the handle portion and the cartridge-receiver front portion. In the third and fourth embodiment, the two-part tool includes a handle portion that is separable from the front cartridge-receiver. Aspects of the invention provide multiple types of separable handles that can be removably attached to the front cartridge-receiver. The separable handle is removable and replaceable with a different type of handle, based on the preferences of the tattoo artist.

Aspects of the invention also include tattoo tool kits that include the tattoo tool and handles and/or accessories.

The tattoo tool of the instant invention saves the tattoo artist time compared to the time required to manually wrap and attach a needle to a grip. The use of a disposable needle cartridge with the inventive tattoo tool increases hygiene (or at least the client's perception of hygiene). Further, the inventive tattoo tool provides convenience for the manual tattoo artist in that disposable needle cartridges are easily available with a variety of pre-determined needle grouping types.

The object of the invention is to provide a tattoo tool which gives an improved performance over the above-described prior art systems and methods.

These and other objects, features, and advantages of the present invention will become more readily apparent from the attached drawings and from the detailed description of the preferred embodiments which follow.

BRIEF DESCRIPTION OF THE SEVERAL VIEWS OF THE DRAWINGS

The preferred embodiments of the invention will hereinafter be described in conjunction with the appended drawings, provided to illustrate and not to limit the invention, where like designations denote like elements.

Like reference numerals refer to like parts throughout the several views of the drawings.

DETAILED DESCRIPTION OF THE INVENTION

Shown throughout the figures, the present invention is directed toward a tattoo tool for use in manual or hand poke tattooing that receives and secures a disposable needle cartridge and that forces the needles of the cartridge into an extended position and maintains them in that position for use.

The first embodiment of the present invention may suitably comprise, consist of, or consist essentially of a single-piece tattoo tool, as seen in FIGS. 1-7.

Figure 6:
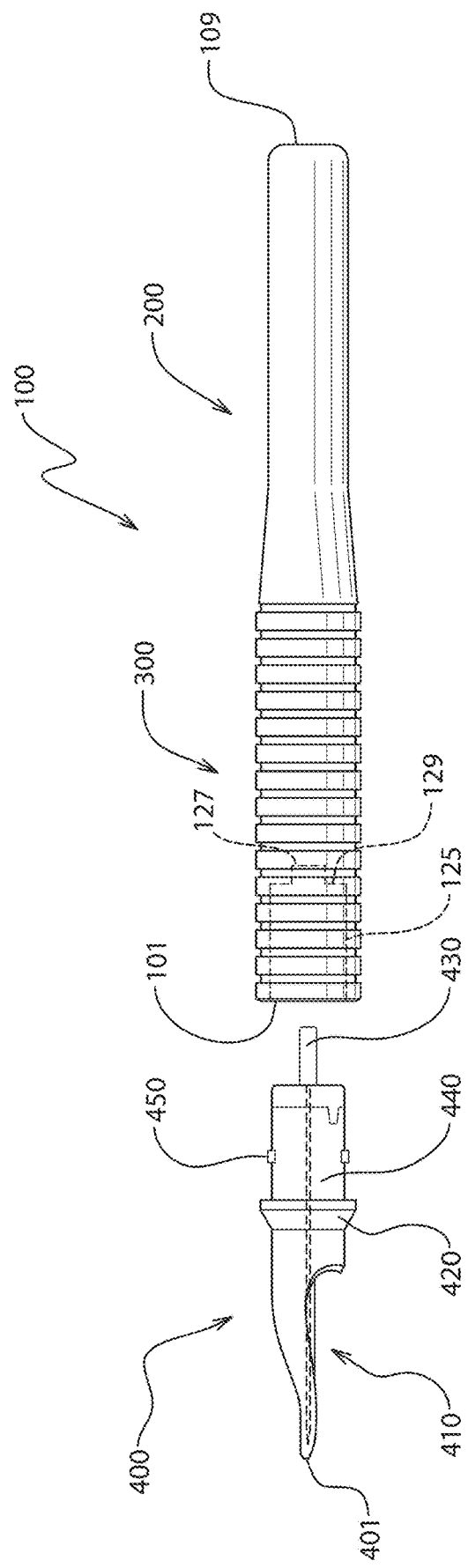
FIG. 6 is a side view of the first tool embodiment of the present invention with the tattoo tool shown aligned with a tattoo disposable needle cartridge to be received.
Figure 7:
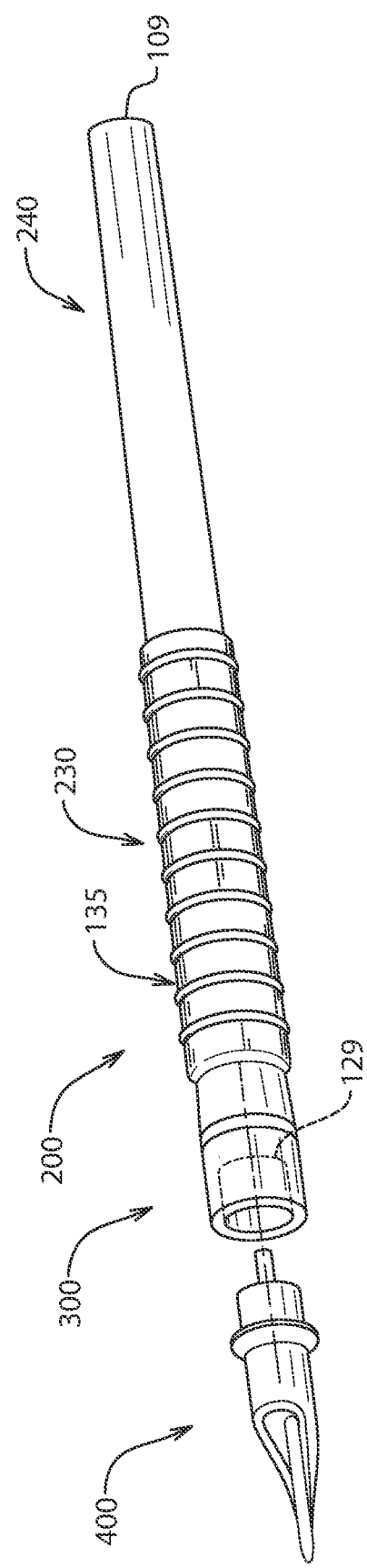
FIG. 7 is a perspective view of an aspect of the first embodiment of the present invention with the tattoo tool shown aligned with a tattoo disposable needle cartridge to be received.

The second embodiment of the present invention may suitably comprise, consist of, or consist essentially of a kit including a single-piece tattoo tool of the first embodiment plus one or more disposable needle cartridges, as seen in FIGS. 6-7.

Figure 8:
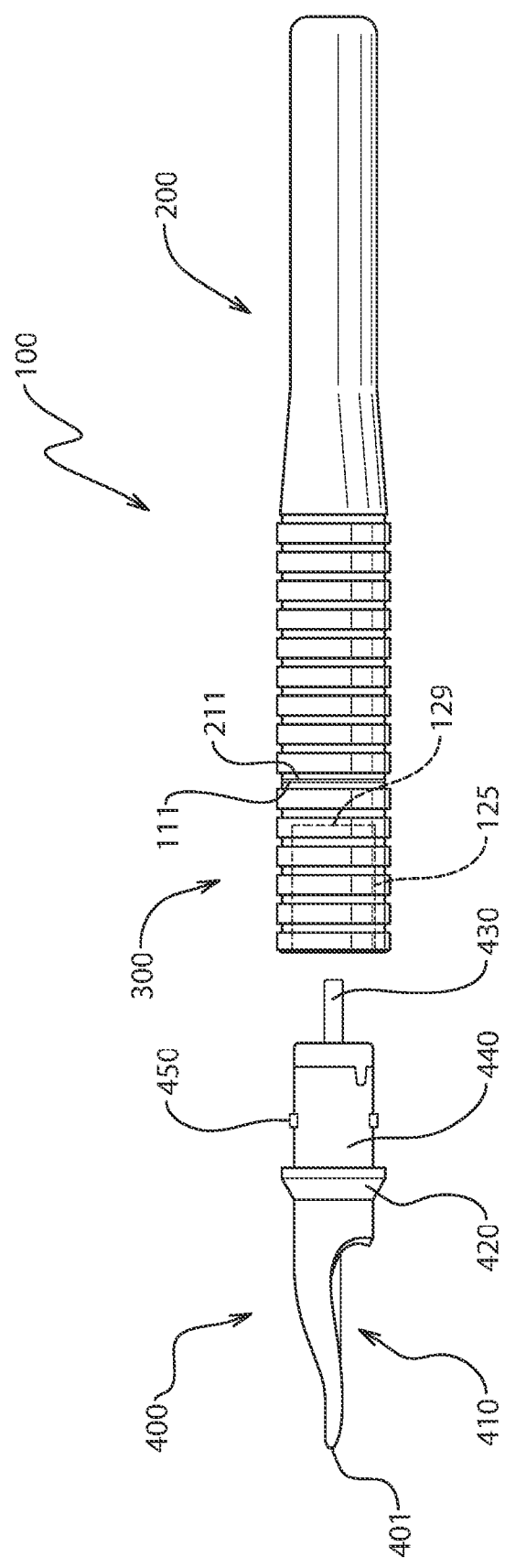
FIG. 8 is a side view of a two-part embodiment of the present invention with the tattoo tool shown aligned with a tattoo disposable needle cartridge to be received.
Figure 9:
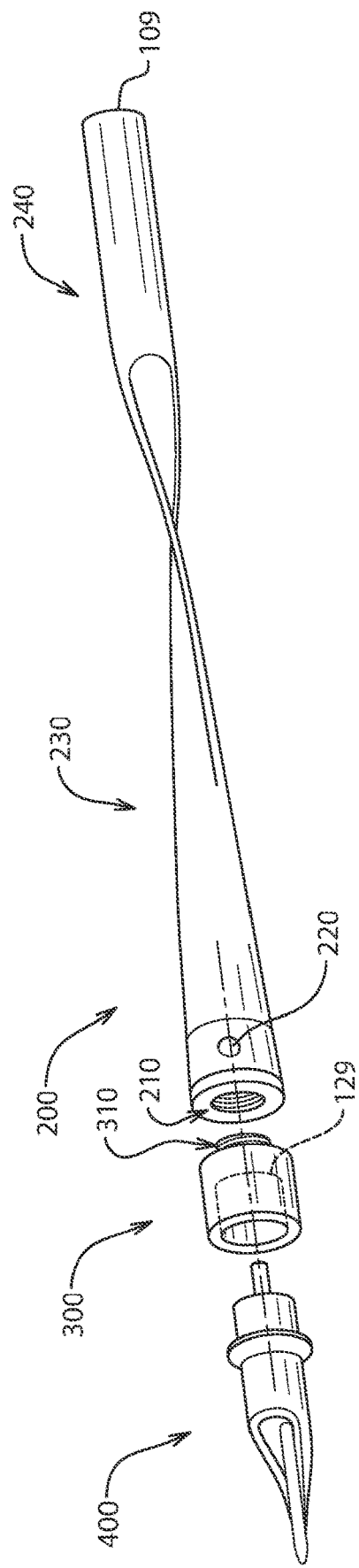
FIG. 9 is a perspective view of a two-part embodiment of the present invention with the tattoo tool shown aligned with a tattoo disposable needle cartridge to be received.
Figure 10:
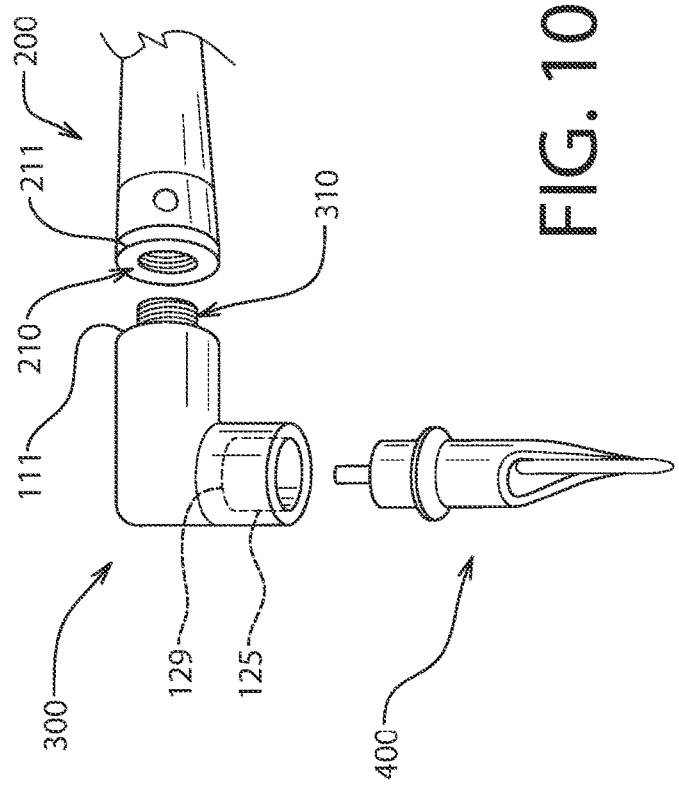
FIG. 10 is a partial perspective view of an aspect of the front portion of an embodiment of the present invention with the front cartridge-receiver shown aligned with a tattoo disposable needle cartridge to be received.

The third embodiment of the present invention may suitably comprise, consist of, or consist essentially of a two-piece tattoo tool with a removable handle, as seen in FIGS. 8-10.

The fourth embodiment of the present invention may suitably comprise, consist of, or consist essentially of a kit including the two-piece tattoo tool of the third embodiment plus one or more disposable needle cartridges, as seen in FIGS. 8-10.

Figure 11:
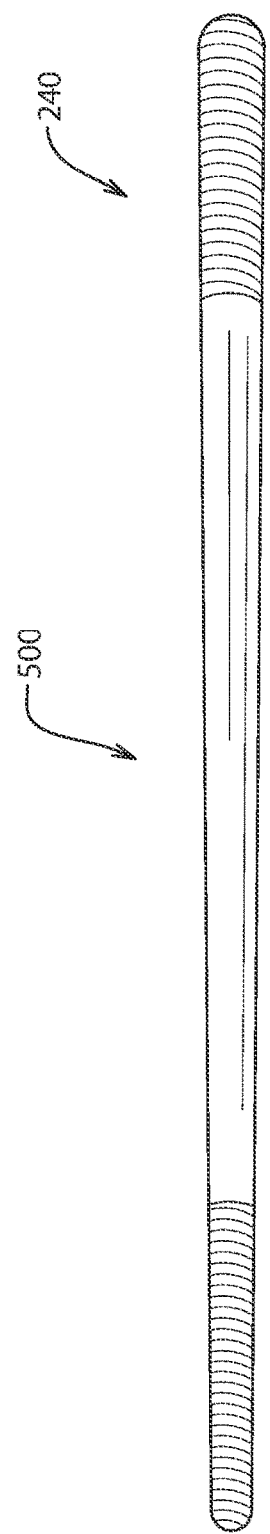
FIG. 11 is a perspective view of a tatau tapping bar of a fifth embodiment of the present invention.

The fifth embodiment of the present invention may suitably comprise, consist of, or consist essentially of a two-piece tattoo tool with a removable handle, a disposable needle cartridge, and a tapping bar, as seen in FIGS. 10-11.

A tattoo tool kit of the present invention may suitably comprise, consist of, or consist essentially of the inventive one-piece tattoo tool with one or more needle cartridges.

An additional tattoo tool kit of the present invention may suitably comprise, consist of, or consist essentially of the inventive two-piece tattoo tool with one removable handle.

A further tattoo tool kit of the present invention may suitably comprise, consist of, or consist essentially of the inventive two-piece tattoo tool with multiple removable handles.

Another tattoo tool kit of the present invention may suitably comprise, consist of, or consist essentially of the inventive two-piece tattoo tool with multiple removable handles and with one or more needle cartridges.

Figure 1:
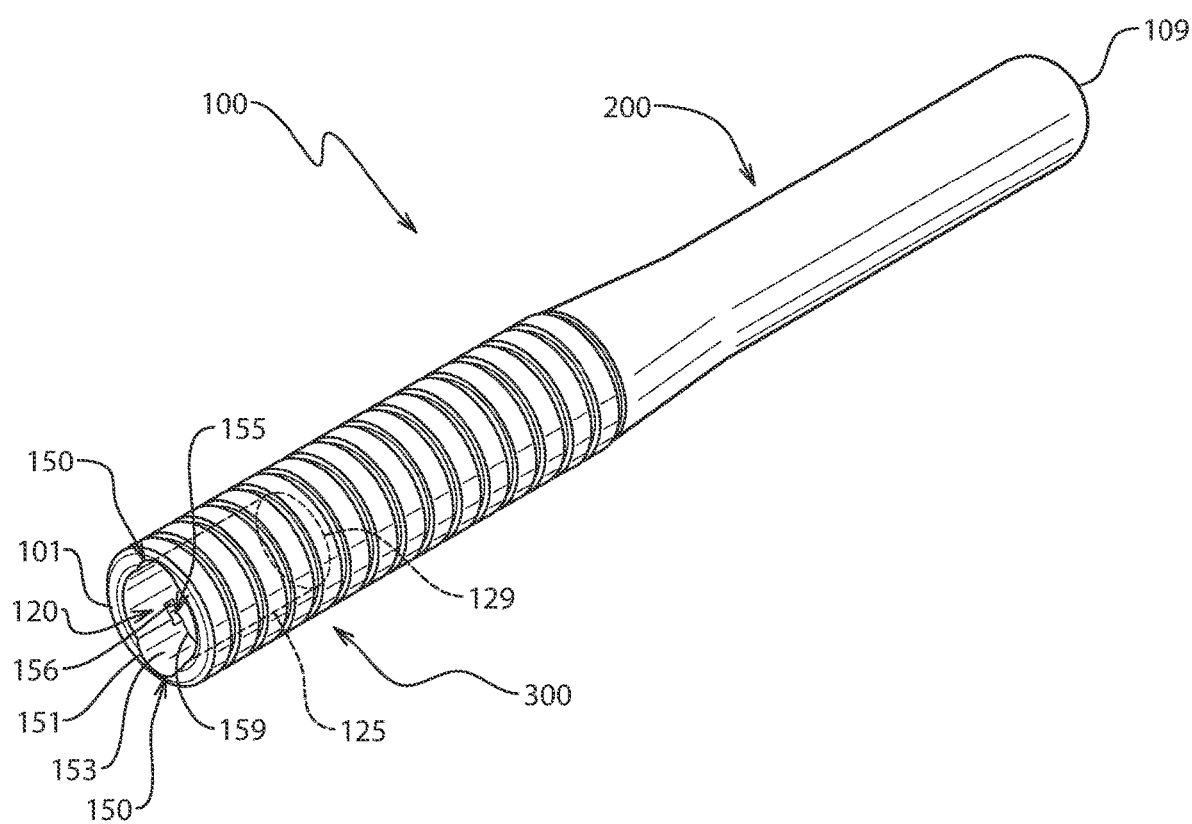
FIG. 1 is a front perspective view of a first embodiment of the present invention.
Figure 2:
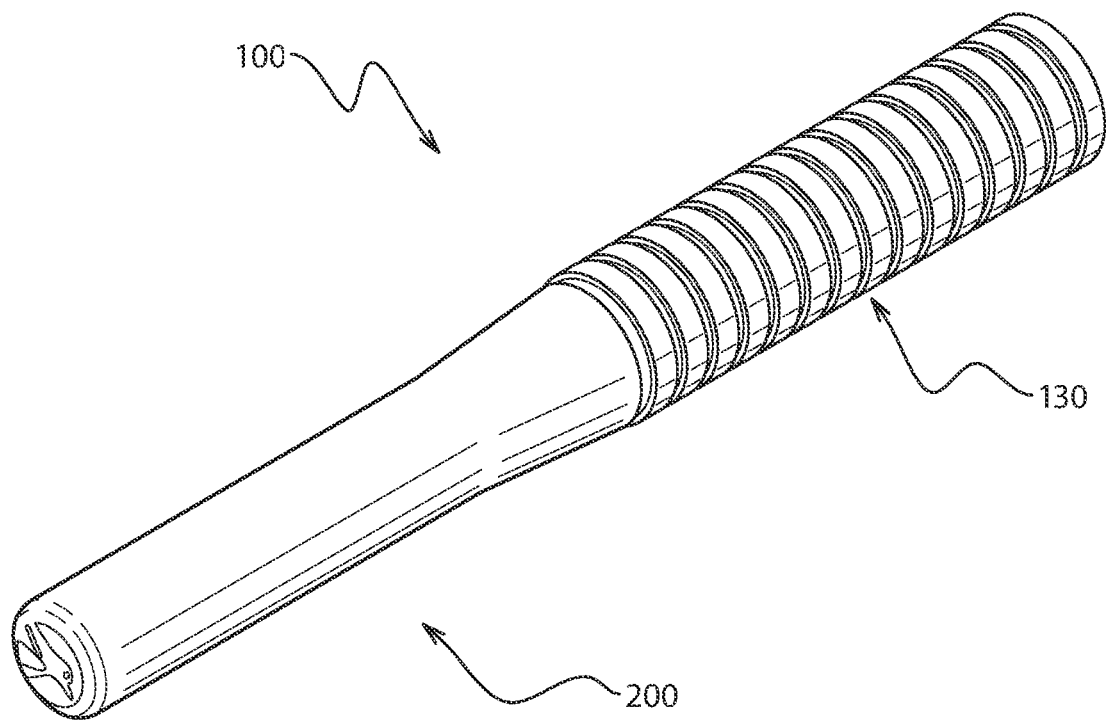
FIG. 2 is a rear perspective view of the first embodiment of the present invention.
Figure 3:
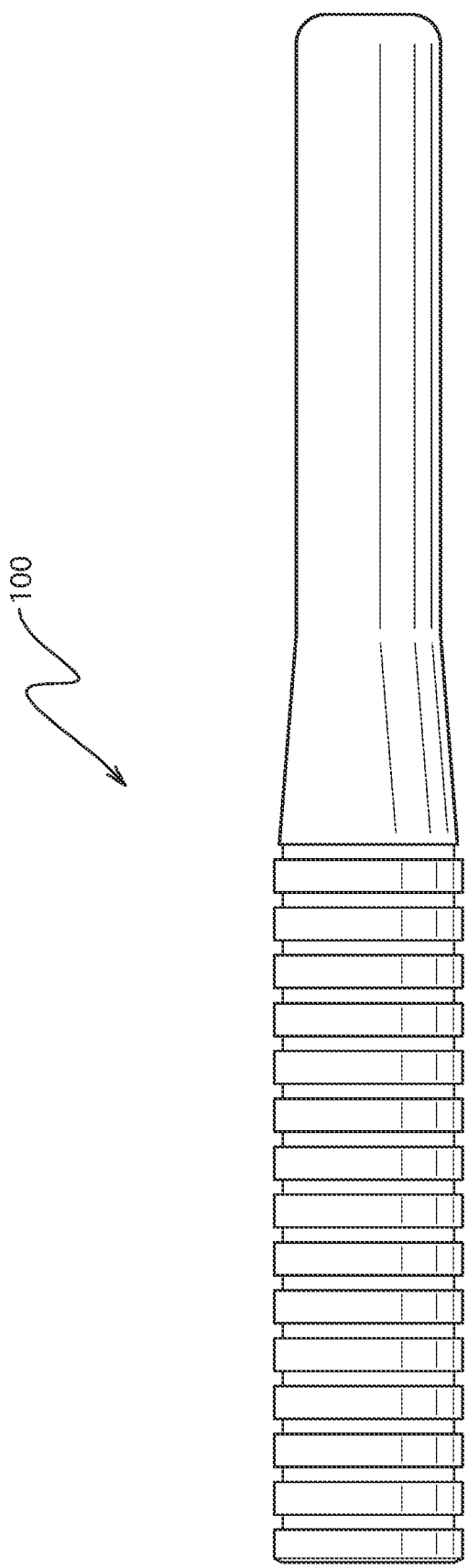
FIG. 3 is a side view of the first embodiment of the present invention.
Figure 4:
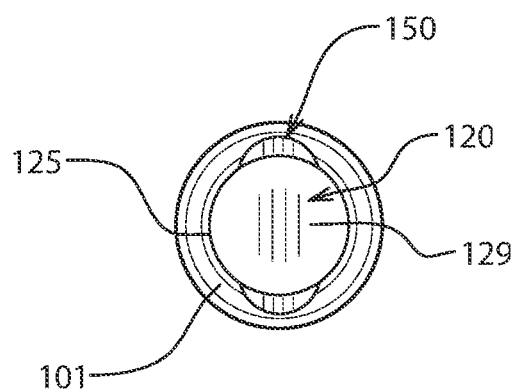
FIG. 4 is a front view of the first embodiment of the present invention.
Figure 5:
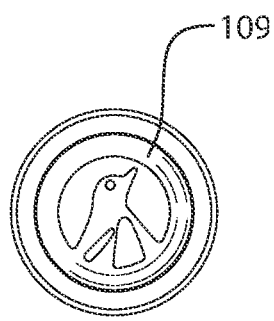
FIG. 5 is a rear view of the first embodiment of the present invention.

Referring now to FIG. 1, a tattoo tool, shown generally as reference number 100, is illustrated in accordance with a first embodiment of the present invention. As shown, the tattoo tool 100 comprises a rear handle portion 200 and a front portion comprising a cartridge-receiver 300. In this first embodiment, the cartridge-receiver 300 and the handle 200 are not separable. The cartridge-receiver 300 and the handle 200 may be formed unitarily or may be formed in multiple parts and fixedly joined.

The tattoo tool 100 extends from a proximal front edge 101 to a distal back edge 109. The front cartridge-receiver 300 extends from the front edge 101 to the intersection with the handle portion 200. The handle 200 extends from the intersection with the cartridge-receiver 300 to the back edge 109.

The front cartridge-receiver 300 comprises a cartridge-receiving concavity 120 that is configured to receive and stably retain a disposable needle cartridge 400 (FIG. 6) while maintaining the needles of the cartridge 400 in an extended position.

The cartridge 400 (FIG. 6), which comprises a conventional cartridge designed for use with a tattoo machine, includes a front casing 410, an abutment 420, a rear casing 440, and a piston 430. In the cartridge's conventional usage, when a cartridge 400 is inserted into an electric tattoo machine, the rear casing 440 is inserted into the front of the machine grip until the abutment 420 is adjacent to the grip front. The cartridge is held firmly within the electric tattoo machine. When in use, the tattoo machine rapidly pushes and retracts the piston 430 reciprocating the needle grouping. The rear casing 440 is configured to be held within a cylindrical concavity in an electric tattoo machine. The conventional cartridge is configured with a cartridge coupling, and the electric tattoo machine is configured with a complementary machine coupling. The cartridge coupling is engaged with the complementary machine coupling. Together the cartridge coupling and the complementary machine coupling function to removably secure the cartridge within the cylindrical concavity of the tattoo machine.

In the inventive tattoo tool 100, the tattoo tool's front cartridge-receiver 300 is configured with a cartridge-receiving coupling 150 that is complementary to the cartridge coupling of the conventional cartridge. Together, the cartridge-receiving coupling 150 and cartridge coupling mechanism function to releasably secure the cartridge 400 within the cylindrical cartridge-receiving concavity 120 of the tattoo tool 100.

Though the cartridge-receiving coupling 150 of the present invention can be configured to correspond to any conventional cartridge coupling, an exemplary cartridge-receiving coupling 150 is presented in FIG. 1, in which the cartridge coupling comprises a projection 450 (FIG. 6) that extends outwardly from the exterior cylindrical wall of the rear casing 440.

As seen in FIG. 1, the open-top cartridge-receiving concavity 120 is substantially defined by a generally cylindrical inner side wall 125 and a solid bottom floor 129. The solid bottom floor 129 may be planar or may be planar with a centrally disposed depression. A planar bottom floor 129 pushes against the cartridge piston 430 to extend the cartridge needle or needle set. In another aspect of the invention, which accommodates some types of cartridges 400 and some tattooing styles or preferences, the floor 129 comprises a center depression 127 (FIG. 6), which is a centrally disposed concave indentation. When the cartridge 400 is installed, the piston 430 descends into this depression 127. This reduces the distance that the needle of the cartridge is extended, which may be advantageous in some types of tattooing, with the use of some types of cartridges, or to meet the desires of particular tattoo artists.

Two opposing lune-shaped concave channels are disposed within the side wall 125 of the cartridge-receiving concavity 120, which are configured to accommodate the two opposing projections 450 disposed on opposite sides of the rear casing 440 of the cartridge 400. Each lune-shaped concave channel is defined by a lune wall 153 that extends from a lune proximal edge 151 to a lune distal edge 159; the concave channel defined by lune wall 153 stops above the concavity bottom floor 129. The lune wall 153 is the lateral surface (the curved part) of the surface area of an imagined right circular cylindrical sector (pie slice-shaped). The height of the right circular cylindrical sector from the lune proximal edge 151 to the lune distal edge 159 corresponds to the distance n the cartridge 400 between the cartridge projection 450 and the distal edge of the cartridge abutment 420. This height is generally less than, or approximately equal to, half of the depth of the concavity 120. Each lune-shaped concave channel, disposed on opposing sides of the cartridge-receiving concavity 120, is configured to receive one of the opposing projections 450 disposed on the opposing sides of the rear casing 440 of the cartridge 400.

Extending to one or to both sides of the bottom of each of the opposing lune-shaped concave channels is a lune-annex cleft 155, which is a separate concave lateral undercut. The lune-annex cleft 155 is defined by cleft walls 156 and is disposed within the side wall 125 adjacent to, and to the side of, the lune distal edge 159. Each lune-annex cleft 155 functions to receive the protruding projection 450 when the cartridge 400 is inserted axially into the cartridge-receiving concavity 120 with the opposing projections 450 traveling down the lune-shaped concave channels, and when the cartridge is then rotated to bring the projection 450 into the lune-annex cleft 155. This removably locks the cartridge 400 in position.

To use the inventive tattoo tool 100 of the first embodiment (with a separately obtained cartridge 400) or to use the kit of the second embodiment (including the tool 100 and the cartridge 400), the tattoo artist axially inserts the needle cartridge 400 into the cartridge-receiving concavity 120. This forces the cartridge piston 430 against the bottom floor 129 of the concavity 120, which, in turn, forces the needle grouping of the cartridge 400 outward with the tips of the needles beyond the cartridge tip 401. The conventional cartridge coupling of the cartridge 400 is then engaged with the cartridge-receiving coupling 150 to lock the cartridge 400 in place. In the exemplary coupling illustrated, the opposing cartridge projections 450 enter the opposing lune-shaped concave channels (each defined by a lune wall 153). Then the cartridge projections 450 are manually rotated in a first direction into the lune-annex cleft 155. In this position, the needles, the tips of which are maintained outside the cartridge tip 401, are used by the tattoo artist in the conventional manner to apply a tattoo to the skin, such as by hand poke tattooing or stick and poke tattooing in which the artist's hand is manually moved to insert the needle tips to the desired depth. If a different needle grouping is desired, such as for shading, the first cartridge 400 can be removed by reversing the installation steps, and a second cartridge 400 can be installed by following the installation steps again. When the tattoo is completed, the tattoo artist removes the cartridge by disengaging the conventional cartridge coupling from the cartridge-receiving coupling 150. In the exemplary coupling illustrated, the cartridge projections 450 are manually rotated in a second direction opposite to the first direction to remove the projections 450 from the lune-annex clefts 155; then the cartridge projections 450 are moved axially up the lune-shaped concave channel. The disposable cartridge 400 is then disposed of in an appropriate manner.

Though the single-piece inventive tattoo tool 100 of the first and second embodiment is illustrated as a front cartridge-receiver 300 to which a handle 200 has been fixedly attached or with which a handle portion 200 has been integrally formed, a single-piece inventive tattoo tool 100 of the first and second embodiment may optionally comprise a front cartridge-receiver 300 with a longer handle 200, such as the handle illustrated in FIG. 7. In this aspect of the invention, the longer handle portion may also be attached fixedly or formed integrally. When the single-piece inventive tattoo tool 100 comprises the shorter handle as shown in FIG. 1, the tattoo tool 100 may range from 4 to 10 inches in length, with 4.5 to 6 inches preferred. When the single-piece inventive tattoo tool 100 comprises the longer handle as shown in FIG. 7, the tattoo tool 100 may range from 10 to 25 inches in length.

Turning to the two-part embodiments, shown in FIGS. 7-10, the tattoo tool 100 is formed with a handle 200 that is separable from the front cartridge-receiver 300. When the cartridge-receiver 300 is engaged with the handle 200, the outer edge 310 of the cartridge-receiver 300 is adjacent to the outer edge 210 of the handle 200, which thus creates a receiver-handle juncture where the two pieces meet. As in the first embodiment, the cartridge-receiving concavity 120 is configured to receive the cartridge 400 with the cartridge-receiving coupling 150 being complementary to the cartridge coupling of the conventional cartridge 400. And, as in the first embodiment, when the cartridge 400 is secured within the cartridge-receiving concavity 120, the piston 430 is depressed by the concavity bottom floor 129, which maintains the needle grouping in the extended position.

However, in the third and fourth embodiments, in contrast to the first and second embodiments, to enable the disassociation and reassociation of the front cartridge-receiver 300 with the handle 200, the cartridge-receiver 300 is configured with a receiver connection mechanism 310 and the handle 200 is configured with a complementary handle connection mechanism 210. These are illustrated in FIGS. 8-9 as a set of complementary threads, but other complementary connectors are within the scope of the invention. For example, the receiver connection mechanism 310 may be configured with a spring-activated and depressible projection. When the cartridge-receiver 300 and the handle 200 are engaged, the receiver connection mechanism 310 may comprise a depressible projection that springs outwardly into a cylindrical open space within the handle. The cylindrical open space includes an aperture into which the projection is extended to secure the cartridge-receiver 300 to the handle 200. When the user desires to change the handle 200, a button 220 (FIG. 9) may be pressed to compress the depressible projection to allow the user to manually remove the cartridge-receiver 200.

Multiple types of replaceable handles 200 are within the scope of the invention. FIG. 8 illustrates a handle type that is shorter (such as from 4 to 10 inches), that may be, for example, used for hand poke tattooing. FIG. 9 illustrates a handle that is longer, such as 10-24 inches in length, for use with tebori tattooing. Each of the types of attachable and removable handles 200 are configured with a complementary handle connection mechanism 210 disposed at the proximal end of the handle 200.

To use the inventive tattoo tool 100 of the third two-part embodiment or the two-part tool kit of the fourth embodiment, a handle 200 of the desired type is selected by the tattoo artist. The handle 200 is engaged with the cartridge-receiver 300 by the use of the complementary connection mechanisms 210, 310. Then, as in the earlier embodiments, a disposable needle cartridge 400 is axially inserted into the cartridge-receiving concavity 120. When fully inserted, the cartridge piston 430 is depressed against the concavity bottom floor 129 to force the needle grouping out past the cartridge tip 401. The conventional cartridge coupling of the cartridge 400 is then engaged with the cartridge-receiving coupling 150 to secure the cartridge 400 in place. The tattooing is performed. When completed, the tattoo artist removes the cartridge by disengaging the conventional cartridge coupling from the cartridge-receiving coupling 150. And the disposable cartridge 400 is disposed of in an appropriate manner.

If the tebori handle 200 of FIG. 9 is selected for use, after attaching the handle 200 to the front cartridge-receiver 300, the needle cartridge 400 is engaged into the tattoo tool's cartridge-receiver 300. Then the tattoo artist manually moves the handle to insert the needles to the desired depth to perform Japanese tebori tattooing.

If the tattoo artist desires to perform Polynesian tatau tattooing, a long tatau handle 200 (similar to the tebori handle of FIG. 9) is attached to the right-angle cartridge-receiver 300 of FIG. 10. A needle cartridge 400 is engaged within the front cartridge-receiver 300. A tatau tapping bar 500 (FIG. 11) is then used to tap on the long handle, which pushes the needles of cartridge 400 to the desired depth on the skin.

In an aspect, the tattoo tool of the present invention is included in a kit. In one aspect, the kit includes a one-piece tattoo tool and at least one disposable needle cartridges. In a second aspect, the kit includes a two-piece tattoo tool with a removable handle. In a third aspect, the kit includes a two-piece tattoo tool with a removable handle and at least one disposable needle cartridge. In a fourth aspect, the kit includes a two-piece tattoo tool with multiple removable handles. In a fifth aspect, the kit includes a two-piece tattoo tool with at least one removable handle, at least one disposable needle cartridge, and a tapping bar.

In the embodiments of the invention, the handle portion 200 may be generally uniform in width or diameter from the proximal part 230 to the distal part 240 of the handle 200, as seen in FIGS. 1-3 and 6-8. Or the handle may vary in width or diameter, as seen in FIG. 9. The handle 200 may be generally cylindrical, or all or parts of it may be shaped in other geometric shapes with a cross section taking the shape of a triangle, rectangle, square, pentagon, octagon, or the like.

In the embodiments of the invention, the front cartridge-receiver 300 may be straight and be in line with the back portion 200, as seen in FIGS. 1-3 and 6-8, or the cartridge-receiver 300 may be angled, as seen in FIG. 10. In the aspect in which the cartridge-receiver 300 takes a right-angle shape, the proximal part of the cartridge-receiver 300 receives the cartridge 400. The distal part of the cartridge-receiver 300 carries the complementary connection mechanism 310 (which corresponds to the complementary connection mechanism 210 of the handle 200). And the right angle is disposed between the proximal and distal parts. FIG. 11 illustrates a tapping bar, such as from 12 to 24 inches in length, which is suitable for tatau style tattooing and may be used to tap on the right-angle cartridge-receiver 300 of FIG. 10.

The tattoo tool 100 of the embodiments of the invention may be formed of any suitable material, such as man-made materials (for example, plastic) or natural products (for example, wood, bamboo, metal, or the like). The cartridge-receiver 300 and the handle 400 may be formed of the same or different materials. In an aspect in which both are formed of the same material, both may be formed integrally of plastic or metal. In an aspect in which they are formed of different materials, the cartridge-receiver 303 may be formed of plastic with the handle 400 formed of wood. In another aspect, the cartridge receiver may be formed of metal with the handle formed of bamboo.

In an aspect of the invention, a removable grip 135 (FIG. 7) is fitted over the handle 200 to add comfort for the tattoo artist. The grip may be formed of natural or manmade flexible material to allow it to be placed onto the handle.

The exterior surfaces of the front cartridge-receiver 300 and the handle 200 may be configured with shapes, textures, or designs. The shapes, textures, or designs on the handle 200 may function not only to aesthetically enhance the look of the tool 100, but they may also increase the artist's ability to grip the handle 200.

Thus, the inventive tattoo tool 100 allows the tattoo artist to preform manual tattooing using conventional disposable needle cartridges, which are designed for machine tattooing. In addition, the two-part variation allows the tattoo artist to select from multiple types of handles to produce a tattoo in any of a variety of tattooing styles.

The invention illustratively disclosed herein suitably may be practiced in the absence of any element which is not specifically disclosed herein.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tattoo tool for use with a tattoo cartridge, said cartridge comprising a proximal cartridge tip, a needle or needle set, a distal piston, and a cartridge-to-tool connection, said tattoo tool comprising:
   a cartridge-receiver disposed at a front end of said tattoo tool and extending rearwardly from a proximal tool front edge; said cartridge-receiver comprising an inner side wall, a solid floor, and a receiver complementary connection that is complementary to said cartridge-to-tool connection; wherein a cartridge-receiving concavity having an open top is defined by said inner side wall, said solid floor, and said receiver complementary connection; wherein said cartridge-receiving concavity extends from said proximal tool front edge rearwardly into said cartridge-receiver to end at said solid floor; wherein, when said cartridge is inserted into said cartridge-receiving concavity, said piston is disposed adjacent to, and depressed by, said solid floor to cause said needle or needle set to be maintained in a constantly extended position with proximal needle tip or tips of said needle or needle set maintained outside said proximal cartridge tip; and
   a handle disposed rearwardly of said cartridge-receiver.

2. The tattoo tool, as recited in claim 1, wherein said cartridge-receiver is detachable from said handle.

3. The tattoo tool, as recited in claim 2, wherein said cartridge-receiver comprises a distal receiver-to-handle connection disposed at a distal portion of said cartridge-receiver, and wherein said handle comprises a proximal handle connection disposed at a proximal portion of said handle that is complementary to said distal receiver-to-handle connection.

4. The tattoo tool, as recited in claim 3, wherein said distal receiver-to-handle connection comprises distal receiver threads, and wherein said proximal handle connection comprises handle threads complementary to said distal receiver threads.

5. The tattoo tool, as recited in claim 3, wherein said cartridge-receiver comprises a receiver proximal portion to receive said tattoo cartridge and a distal receiver portion; and wherein said receiver proximal portion forms a substantially ninety-degree angle with said distal receiver portion.

6. The tattoo tool, as recited in claim 2, wherein said handle comprises a tebori handle.

7. The tattoo tool, as recited in claim 2, wherein said handle comprises a tatau handle.

8. The tattoo tool, as recited in claim 2, wherein said receiver complementary connection comprises:
two opposing lune-shaped concave regions disposed within said inner side wall and extending from a lune proximal edge to a lune distal edge; and
a lune-annex cleft formed by a lateral undercut within said inner side wall adjacent to said lune distal edge of each of said two opposing lune-shaped concave regions.

9. The tattoo tool, as recited in claim 1, wherein said handle comprises a tebori handle.

10. The tattoo tool, as recited in claim 1, wherein said handle comprises a tatau handle.

11. The tattoo tool, as recited in claim 1, wherein said receiver complementary connection comprises:
two opposing lune-shaped concave regions disposed within said inner side wall and extending from a lune proximal edge to a lune distal edge; and
a lune-annex cleft formed by a lateral undercut within said inner side wall adjacent to said lune distal edge of each of said two opposing lune-shaped concave regions.

12. The tattoo tool, as recited in claim 1, wherein said solid floor is planar.

13. The tattoo tool, as recited in claim 1, wherein said solid floor is flat with a center depression.

14. A method to assemble a tattoo tool, said tattoo tool comprising: (a.) a handle and (b.) a cartridge-receiver disposed at a front end of said tattoo tool and extending rearwardly from a proximal tool front edge; said cartridge-receiver comprising an inner side wall, a solid floor, and a receiver complementary connection that is complementary to a tattoo cartridge connection; wherein a cartridge-receiving concavity having an open top is defined by said inner side wall, said solid floor, and said receiver complementary connection; wherein said cartridge-receiving concavity extends from said proximal tool front edge rearwardly into said cartridge-receiver to end at said solid floor; the method comprising:
aligning a rear casing of a disposable needle cartridge with said cartridge-receiving concavity of tattoo tool;
aligning a first and a second projection extending outwardly from said rear casing with a first and a second lune-shaped concave channel within said cartridge-receiving concavity;
fully inserting said rear casing into said cartridge-receiving concavity to engage a piston of said disposable needle cartridge with said solid floor of said cartridge-receiving concavity; wherein said piston is depressed and a needle grouping of said cartridge is extended outwardly and maintained a constantly extended position with proximal needle tips of said maintained outside a proximal cartridge tip; and
twisting said disposable needle cartridge to removably secure said cartridge in said cartridge-receiving concavity.

15. The method to assemble a tattoo tool, as recited in claim 14, wherein said solid floor comprises a planar floor.

16. The method to assemble a tattoo tool, as recited in claim 14, wherein said solid floor comprises a flat floor with a centrally disposed depression; the method further comprising:
inserting said piston into said centrally disposed depression.

17. The method to assemble a tattoo tool, as recited in claim 14, wherein said cartridge-receiving concavity is disposed within a front portion of said tattoo tool; the method further comprising:
attaching said handle to said front portion.

18. The method to assemble a tattoo tool, as recited in claim 17, further comprising:
threadingly engaging said handle with said front portion.

19. A tattoo kit, comprising:
a disposable needle cartridge; said cartridge comprising a distal piston, a proximal cartridge tip, a needle or needle set, and a cartridge-to-tool connection; and
a tattoo tool comprising:
(a.) a cartridge-receiver disposed at a front end of said tattoo tool and extending rearwardly from a proximal tool front edge; said cartridge-receiver comprising an inner side wall, a solid floor, and a receiver complementary connection that is complementary to said cartridge-to-tool connection; wherein a cartridge-receiving concavity has an open top and is defined by said inner side wall, said solid floor, and said receiver complementary connection; wherein said cartridge-receiving concavity extends from said proximal tool front edge rearwardly into said cartridge-receiver to end at said solid floor; and
a handle disposed at a rear end of said tattoo tool;
wherein, upon fully inserting said disposable needle cartridge into said cartridge-receiving concavity, said distal piston is depressed by said solid floor to cause said needle or needle set to be maintained in a constantly extended position with proximal needle tips of said needle or needle set maintained outside said proximal cartridge tip.

20. The tattoo kit as recited in claim 19, wherein said cartridge-receiver is detachable from said handle;
wherein said cartridge-receiver comprises cartridge-receiver threads disposed at a distal portion of said cartridge-receiver; and
wherein said handle comprises a complementary handle threads disposed at a proximal portion of said handle.

\* \* \* \* \*